(12) United States Patent
Sun et al.

(10) Patent No.: US 8,436,608 B2
(45) Date of Patent: May 7, 2013

(54) EDDY CURRENT INSPECTION SYSTEM AND METHOD

(75) Inventors: Haiyan Sun, Niskayuna, NY (US); Yuri Alexeyevich Plotnikov, Niskayuna, NY (US); Changting Wang, Niskayuna, NY (US); Shridhar Champaknath Nath, Niskayuna, NY (US); Aparna Chakrapani Sheila-Vadde, Bangalore (IN)

(73) Assignee: General Electric Company, Niskayuna, NY (US)

( * ) Notice: Subject to any disclaimer, the term of this patent is extended or adjusted under 35 U.S.C. 154(b) by 797 days.

(21) Appl. No.: 12/563,403

(22) Filed: Sep. 21, 2009

(65) Prior Publication Data

US 2011/0068784 A1  Mar. 24, 2011

(51) Int. Cl.
*G01N 27/82* (2006.01)
*G01R 33/14* (2006.01)
*G01R 33/00* (2006.01)

(52) U.S. Cl.
USPC .......................... 324/240; 324/222; 324/260

(58) Field of Classification Search .................. 324/222, 324/234, 236–240, 242, 251, 260, 262, 659, 324/681, 686, 690
See application file for complete search history.

(56) References Cited

U.S. PATENT DOCUMENTS

| | | | |
|---|---|---|---|
| 3,689,828 A | 9/1972 | Kurose et al. | |
| 3,697,866 A | 10/1972 | Kanda et al. | |
| 4,207,520 A | 6/1980 | Flora et al. | |
| 5,047,719 A | 9/1991 | Johnson et al. | |
| 5,648,611 A | 7/1997 | Singh et al. | |
| 6,563,308 B2 | 5/2003 | Nagano et al. | |
| 6,803,757 B2 | 10/2004 | Slates | |
| 7,206,706 B2 | 4/2007 | Wang et al. | |
| 7,233,867 B2 | 6/2007 | Pisupati et al. | |
| 7,336,069 B2 | 2/2008 | Perriard | |

(Continued)

FOREIGN PATENT DOCUMENTS

| | | |
|---|---|---|
| DE | 4041392 A1 | 6/1992 |
| EP | 0100009 A1 | 2/1984 |
| JP | 9089845 A | 4/1997 |
| JP | 2006337250 A | 12/2006 |

OTHER PUBLICATIONS

PCT/US2010/042684 Search Report, Oct. 14, 2010.

(Continued)

*Primary Examiner* — Joshua Benitez Rosario
(74) *Attorney, Agent, or Firm* — Penny A. Clarke

(57) ABSTRACT

A multi-frequency eddy current (MFEC) inspection system is provided for inspection of case hardening depth on a part. The MFEC inspection system comprises a generator configured to generate one or more multi-frequency excitation signals and an eddy current probe configured to be disposed at one side of the part. The eddy current probe comprises one or more drivers and one or more pickup sensors. The one or more drivers are configured to receive the one or more multi-frequency excitation signals to induce eddy currents in the part. The one or more pickup sensors are configured to detect the induced eddy currents within a local area of the part to generate one or more multi-frequency response signals. The MFEC system further comprises a processor configured to receive the one or more multi-frequency response signals for processing to determine a case hardening depth of the local area of the part. A pulse eddy current inspection system and an eddy current inspection method are also presented.

18 Claims, 7 Drawing Sheets

U.S. PATENT DOCUMENTS

| | | | |
|---|---|---|---|
| 7,385,392 B2 | 6/2008 | Schlicker et al. | |
| 7,423,423 B2 | 9/2008 | Becker et al. | |
| 7,443,177 B1 * | 10/2008 | Bowler | 324/715 |
| 7,518,359 B2 | 4/2009 | Wang et al. | |
| 8,207,731 B2 * | 6/2012 | Moskalenko | 324/233 |
| 8,274,279 B2 * | 9/2012 | Gies | 324/240 |

OTHER PUBLICATIONS

N. Nakagawa et al., "Unconventionally High and Low Frequency Eddy Current Methods for Material Surface Characterizations," Review of Quantitative Nondestructive Evaluation, vol. 29, Jul. 26, 2009, pp. 1471-1478.

M.J. Johnson et al., "Pulsed Eddy-Current Measurements for the Characterization of thin Layers and Surface Treatments," Review of Progress in quantitative Nondestructive evaluation, vol. 17, Aug. 1, 1997, pp. 251-257.

H. Sun et al., "Eddy current Measurements on Case Hardened Steel," Review of Quantitative Nondestructive Evaluation, AIP Conference Proceedings, vol. 21, No. 6158, Jul. 29, 2001, pp. 1561-1568.

DE4041392A1 Abstract, June 25, 1992.

Ibg NDT Systems—Eddy Current Test Systems http://www.ibgndt.com/eddy-current-crack-detection-flaw.htm; downloaded Aug. 17, 2009.

J. Cuffe et al., "Eddy Current Measurement of Case Hardened Depth of Steel Components," 17th World Conference on Nondestructive Testing, 7 Pages, Oct. 2008, Shanghai, China.

"Eddy Current Measurements on Case-Hardened Steel." http//www.cnde.iastate.edu/cnde_news/e-newsletter0201/PDF%20files/Eddy%20Current%20Measurements.pdf; downloaded Jun. 9, 2009.

JP9089845 Abstract, Apr. 4, 1997.

JP2006337250 Abstract, Dec. 14, 2006.

EP0100009 Abstract, Feb. 8, 1984.

* cited by examiner

EDDY CURRENT INSPECTION SYSTEM AND METHOD

BACKGROUND

This invention relates generally to inspection systems and methods. More particularly, this invention relates to eddy current inspection systems and methods for inspection of case hardening depths of parts.

Parts, such as crankshafts, valves, gears, piston cylinders are often subjected to heat treatment and carburization to produce case hardening layers on surfaces thereof so as to improve resistance to wear. Different parts generally have different requirements for case hardening depths of the case hardening layers thereon. Thus, it is necessary to perform inspection to determine whether the case hardening depths on such parts are suitable for quality control.

Nondestructive evaluation (NDE) techniques are being pursued to inspect case hardening depths of parts. Since electrical conductivity and magnetic permeability in case hardening regions are different from those in other regions, eddy current inspection techniques can be employed to inspect the case hardening depths of the parts.

In some applications, eddy current methods are used to inspect the case hardening depths of cylindrical objects using encircling probes. However, because the eddy current probes are mounted around the parts, they may merely provide information about average case hardening depths of such parts instead of local information. In addition, such eddy current probes are generally used for inspection of case hardening depths of cylindrical parts, and may not be suitable for inspecting case hardening depths of parts having other shapes.

Therefore, there is a need for a new and improved eddy current inspection system and method for inspection of case hardening depths of parts.

BRIEF DESCRIPTION

A multi-frequency eddy current (MFEC) inspection system for inspection of case hardening depth on a part is provided in accordance with one embodiment of the invention. The MFEC inspection system comprises a generator configured to generate one or more multi-frequency excitation signals and an eddy current probe configured to be disposed at one side of the part. The eddy current probe comprises one or more drivers and one or more pickup sensors. The one or more drivers are configured to receive the one or more multi-frequency excitation signals to induce eddy currents in the part. The one or more pickup sensors are configured to detect the induced eddy currents within a local area of the part to generate one or more multi-frequency response signals. The MFEC system further comprises a processor configured to receive the one or more multi-frequency response signals for processing to determine a case hardening depth of the local area of the part.

Another embodiment of the invention provides a pulse eddy current (PEC) inspection system for inspection of case hardening depth on a part. The PEC inspection system comprises a pulse generator configured to generate one or more pulse excitation signals and an eddy current probe configured to be disposed at one side of the part. The eddy current probe comprises one or more drivers and one or more pickup sensors. The one or more drivers are configured to receive the one or more pulse excitation signals to induce eddy currents in the part. The one or more pickup sensors are configured to detect the induced eddy currents within a local area of the part to generate one or more multi-frequency response signals. The PEC system further comprises a processor configured to receive the one or more multi-frequency response signals for processing to determine a case hardening depth of the local area of the part.

Another aspect of the invention further provides a method for inspection of case hardening depth of a part. The method comprises generating one or more multi-frequency excitation signals or one or more pulse excitation signals, providing an eddy current probe configured to be disposed at one side of the part to receive the one or more multi-frequency excitation signals or the or one or more pulse excitation signals and output one or more multi-frequency response signals, and processing the one or more multi-frequency response signals to determine the case hardening depth of a local area of the part. The eddy current probe comprises one or more drivers and one or more pickup sensors. The one or more drivers are configured to receive the one or more multi-frequency excitation signals to induce eddy currents in the part. The one or more pickup sensors are configured to detect the induced eddy currents within the local area of the part and to generate the one or more multi-frequency response signals.

BRIEF DESCRIPTION OF THE DRAWINGS

The above and other aspects, features, and advantages of the present disclosure will become more apparent in light of the subsequent detailed description when taken in conjunction with the accompanying drawings in which.

DETAILED DESCRIPTION OF THE INVENTION

Embodiments of the present disclosure are described herein with reference to the accompanying drawings. In the subsequent description, well-known functions or constructions are not described in detail to avoid obscuring the disclosure in unnecessary detail.

Figure 1:
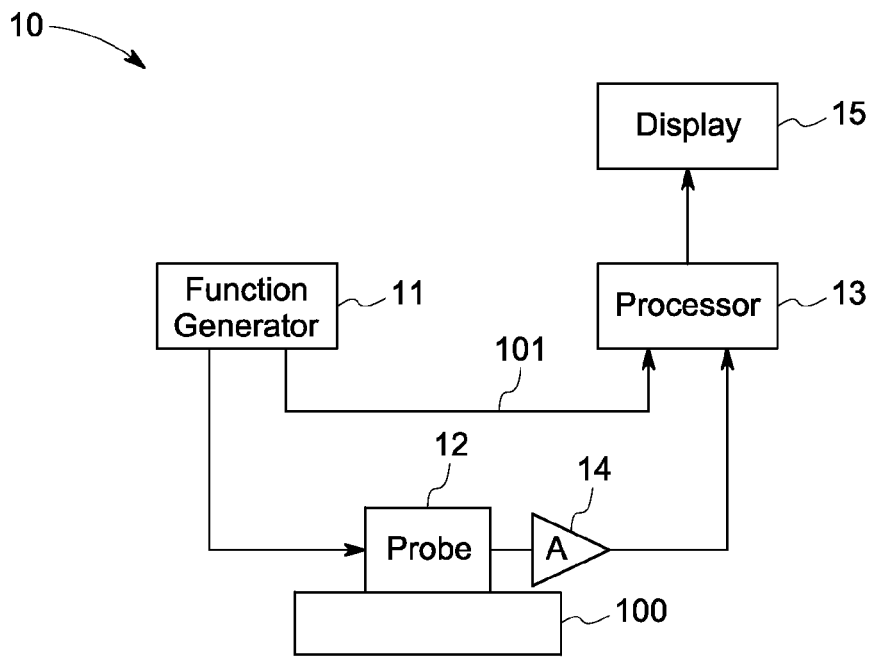
FIG. 1 is a schematic diagram of an eddy current inspection system in accordance with one embodiment of the invention.

FIG. 1 is a schematic diagram of an eddy current inspection system 10 for inspection of a part 100 in accordance with one embodiment of the invention. As used herein, the term "part" may indicate any object suitable for inspection, including but not limited to articles, components, structures, test specimens, and the like. In some applications, the part 100 may be subjected to one or more hardening processes, such as heat treatment processes and carburization processes, so that one or more hardened layers may be formed on surface(s) of the part 100 to improve resistance thereof to wear. For some arrangements, the part 100 comprises a cylindrical shape. In other examples, the part 100 may comprises other shapes, such as a rectangular shape or other irregular shapes.

In some embodiments, the eddy current inspection system 10 may be configured to inspect case hardening depth(s) of the part 100. For the arrangement in FIG. 1, the eddy current inspection system 10 comprises a multi-frequency eddy current (MFEC) inspection system. As indicated in FIG. 1, the MFEC system 10 comprises a function generator 11, an eddy current probe 12, and a processor 13.

In some embodiments, the function generator 11 is configured to generate and output one or more multi-frequency excitation signals into the eddy current probe 12. The eddy current probe 12 is configured to receive the one or more multi-frequency excitation signals and to induce eddy currents in the part 100 to generate one or more multi-frequency response signals. The processor 13 is configured to analyze the one or more multi-frequency response signals to determine the case hardening depth of the part 100, for example, using a multi-frequency phase analysis (MFPA) algorithm. Other descriptions of the processor 13 may be found, for example, in U.S. Pat. No. 7,206,706, which is hereby incorporated by reference in its entirety.

In some applications, the processor 13 may comprise a lock-in amplifier for analyzing the input multi-frequency response signals. Accordingly, as depicted in FIG. 1, in one non-limiting example, the function generator 11 further generates reference signals 101 with the same frequencies as the respective multi-frequency excitation signals to demodulate the response signals in the lock-in amplifier 13. In certain examples, the reference signals may not be employed.

For the illustrated example, the MFEC system 10 further comprises an amplifier 14 disposed between the eddy current probe 12 and the processor 13 for amplifying the multi-frequency response signals before the response signals are input into the processor 13. Additionally, the MFEC system 10 may further comprise a display 15, such as a liquid crystal display (LCD) connected to the processor 13 to display information of the case hardening depth on the part 100. The invention is not limited to any particular type of display. In some examples, the amplifier 14 may not be employed. The function generator 11, the processor 13, and/or the display 15 may be replaced with a multifrequency eddy current device.

Figure 2:
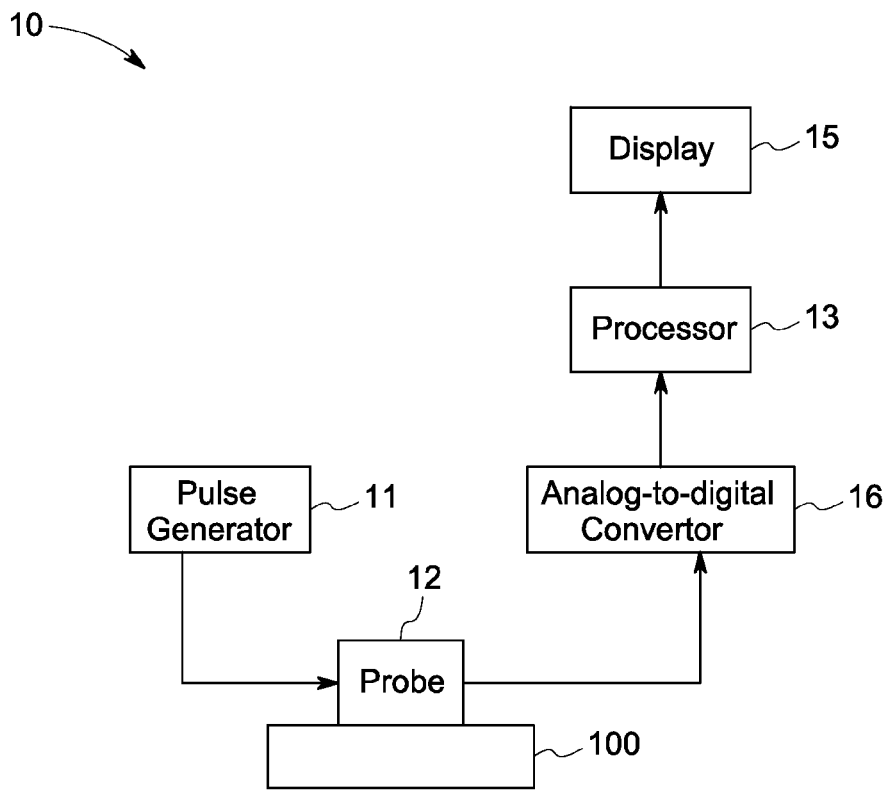
FIG. 2 is a schematic diagram of the eddy current inspection system in accordance with another embodiment of the invention.

FIG. 2 is a schematic diagram of the eddy current inspection system 10 in accordance with another embodiment of the invention. For the ease of illustration, the same numerals in FIGS. 1 and 2 may indicate similar elements. For the arrangement illustrated in FIG. 2, the eddy current inspection system 10 comprises a pulse eddy current (PEC) system.

Similar to the arrangement in FIG. 1, the PEC system 10 comprises a pulse generator 11 that is configured to generate and output a plurality of pulse excitation signals supplying different frequencies into an eddy current probe 12. The eddy current probe 12 is configured to receive the pulse excitation signals and to induce eddy currents in the part 100 so as to generate one or more multi-frequency response signals for determination of the case hardening depth on the part 100. Further, the PEC system 10 comprises an analog-to-digital converter 16 that is configured to digitize the response signals from the eddy current probe 12 and to supply the digitized response signals to a processor 13. The processor 13 is configured to analyze the digitized response signals to determine the case hardening depth of a local area of the part 100 using the multi-frequency phase analysis algorithm, for example. In certain applications, the analog-to-digital converter 16 may not be employed.

In some examples, the PEC system 10 may comprise a display 15, such as a liquid crystal display (LCD) connected to the processor 13 to display the data of the case hardening depth of the part 100.

It should be noted that the present invention is not limited to any particular processor for performing the processing tasks of the invention. The term "processor", as that term is used herein, is intended to denote any machine capable of performing the calculations, or computations, necessary to perform the tasks of the invention. The term "processor" is intended to denote any machine that is capable of accepting a structured input and of processing the input in accordance with prescribed rules to produce an output, as will be understood by those skilled in the art. It should also be noted that the phrase "configured to" as used herein indicates that processor is equipped with a combination of hardware and software for performing the tasks of the invention, as will be understood by those skilled in the art. Moreover, the suffix "(s)" as used herein is usually intended to include both the singular and the plural of the term that it modifies, thereby including one or more of that term.

FIGS. 3-5 and 11-13 are schematic diagrams of example arrangements of the eddy current probe 12 and the part 100 illustrating the determination of the case hardening depth on the part 100. In embodiments of the invention, the eddy current probe 12 may comprise a reflective probe for inspection of the case hardening depth(s) for one or more local areas of the part 100. In addition, it should be noted that the arrangement in FIGS. 3-5 and 11-13 are merely illustrative. The same numerals in FIGS. 3-5 and 11-13 may indicate similar elements.

Figure 3:
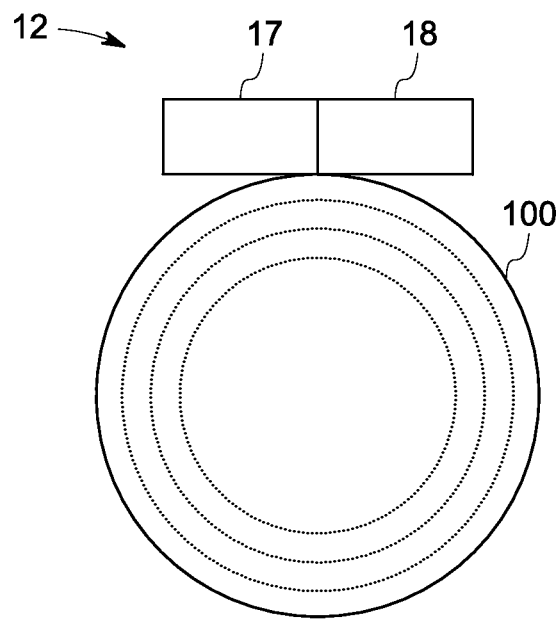
FIGS. 3-7 and 11-13 are schematic diagrams of example arrangements of an eddy current probe and a part in accordance with various embodiments of the invention.
Figure 11:
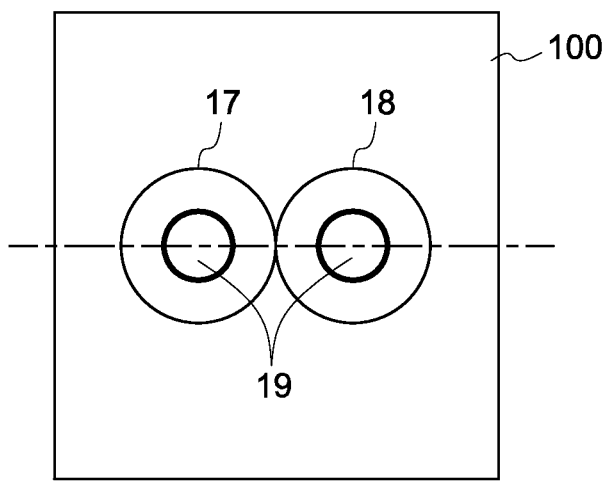

FIGS. 3 and 11 are schematic diagrams of a side view and a top view of an example arrangement of the eddy current probe 12 and the part 100. For the arrangement illustrated in FIGS. 3 and 11, the eddy current probe 12 is disposed at one side of the part 100 and comprises a driver 17 and a pickup sensor 18 located aside the driver 17. In certain embodiments, both the driver 17 and the pickup sensor 18 may be formed with windings. In non-limiting examples, the pickup sensor 18 may comprise a solid-state magnetic sensor including, but not limited to an anisotropic magnetoresistance (AMR) sensor, a giant magnetoresistance (GMR) sensor, a tunneling magnetoresistance (TMR), an extraordinary magnetoresistance (EMR) sensor, a giant magnetoimpedance (GMI) or a Hall sensor.

In embodiments of the invention, the driver 17 is configured to receive the excitation signals having a plurality of different frequencies from the function generator or the pulse generator 11 (shown in FIGS. 1-2) to induce the eddy currents in the part 100. The pickup sensor 18 is configured to detect the eddy currents induced in the part 100 to generate and output one or more response signals into the processor 13 for processing.

For the example arrangement, both the driver 17 and the pickup sensor 18 have cylindrical hollow shapes and the driver 17 is located adjacent to the pickup sensor 18. Bottom surfaces (not labeled) of the driver winding 17 and the pickup sensor 18 are located within the same plane to face a local area (not labeled) on the part 100 for determination of the case hardening depth thereof.

In some examples, the driver 17 and the pickup sensor 18 may contact the part 100 to inspect the case hardening depth on the local area thereon. Two magnet cores 19 including, but not limited to ferrite cores, may be disposed within the driver 17 and the pickup sensor 18 respectively to enhance the inspection of the case hardening depth. In certain applications, the driver 17 and the pickup sensor 18 may be spatially separated from the part 100. In other examples, the magnet core(s) 19 may not be provided within the driver 17 and/or the pickup sensor 18.

In certain applications, the driver 17 may have a rectangular shape. For this arrangement, the cylindrical pickup sensor 18 may still have a cylindrical shape and be disposed aside the rectangular driver 17. Similar to the arrangement in FIGS. 3 and 11, the bottom surfaces of the rectangular driver winding 17 and the cylindrical pickup sensor 18 are located within the same plane to face the part 100. Additionally, magnet core(s) may or may not be provided within the driver 17 and/or the pickup sensor 18.

Figure 4:
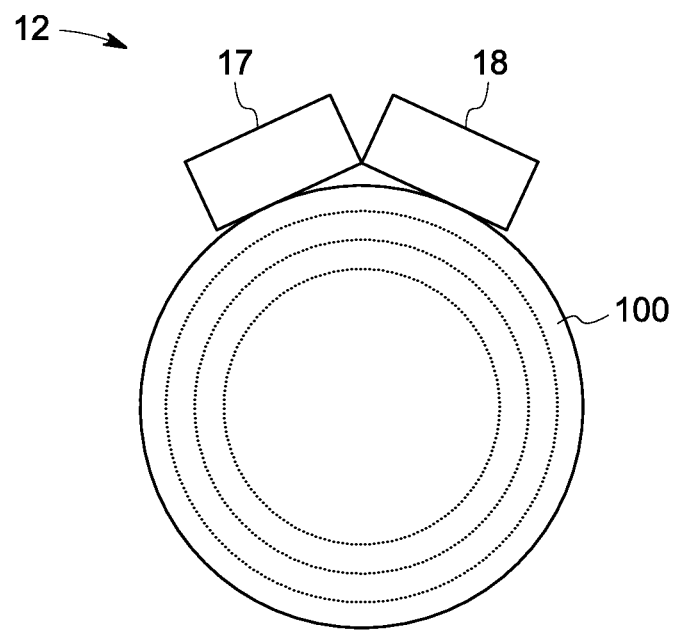
Figure 12:
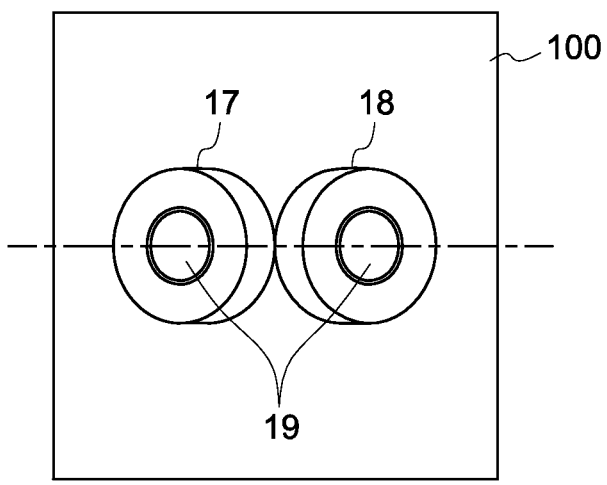

FIGS. 4 and 12 are schematic diagrams of a side view and a top view of another example arrangement of the eddy current 12 and the part 100. Similar to the arrangement in FIGS. 3 and 11, as depicted in FIGS. 4 and 12, both the driver 17 and the pickup sensor 17 have cylindrically hollow shapes. The arrangements in FIGS. 3 and 11, and 4 and 12 differ in that the driver 17 and the pickup sensor 18 in FIGS. 4 and 12 are disposed with bottom surfaces thereof tangential with the circumference of the part 100 to inspect the case hardening depth of a local area of the part 100. That is, the bottom surfaces of the driver 17 and the pickup sensor 18 have an angle therebetween, which indicates that the bottom surfaces of the driver 17 and the pickup sensor 18 are not coplanar. Additionally, the magnet cores 19 may or may not be provided within the driver 17 and the pickup sensor 18.

In other examples, both the driver 17 and the pickup sensor 18 may have rectangular shapes. Similar to the arrangement in FIGS. 4 and 12, the bottom surfaces of the rectangular driver 17 and the rectangular pickup sensor 18 may be tangential to the circumference of the part 100.

Alternatively, similar to the arrangement in FIGS. 3 and 11, the bottom surfaces of the rectangular driver 17 and the rectangular pickup sensor 18 may be located within the same plane to face the circumference of the part 100. In certain applications, when the part 100 has a rectangular shape, the rectangular driver 17 and the rectangular pickup sensor 18 may be located horizontally at the local area of the part 100.

Figure 5:
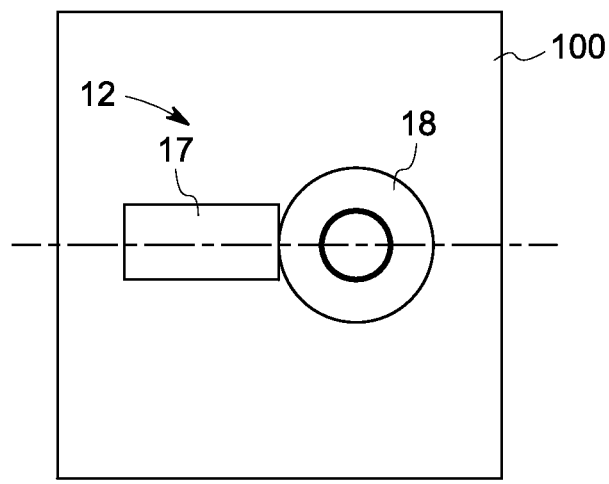
Figure 13:
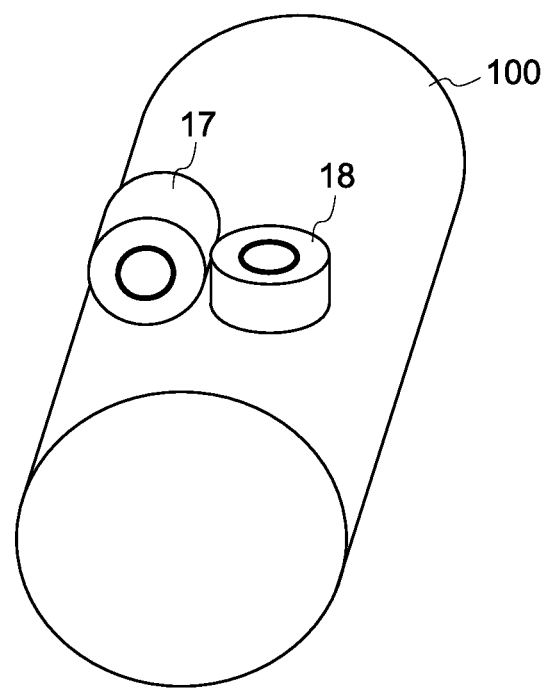

FIGS. 5 and 13 are schematic diagrams of a top view and a perspective view of an example arrangement of the eddy current 12 and the part 100 in accordance with yet another embodiment of the invention. The arrangement in FIGS. 5 and 13 is similar to the arrangements in FIGS. 3 and 11, and 4 and 12. The arrangements in FIGS. 3 and 11, 4 and 12, and 5 and 13 differ in that the driver 17 in FIGS. 5 and 13 is disposed near the local area with a driver axis (not labeled) thereof parallel to an axis (not labeled) of the part 100 for induction of the eddy currents in the part 100. That is, a side surface of the driver 17 may face and be in contact with the local area of the part 100 instead of the bottom surface thereof. Further, the pickup sensor 18 in FIGS. 5 and 13 is adjacent to the driver 17 and is disposed near the local area with its axis perpendicular to the axis of the driver 17.

For other arrangements, the pickup sensor 18 may be disposed with its side surface facing the part 100 and with its axis parallel to the axis of the part 100. The driver 17 may be disposed with its axis perpendicular to the axis of the pickup sensor 18. Additionally, the magnet core(s) may or may not be provided.

In non-limiting examples, the driver and/or the pickup sensor may have oval shapes. The surfaces of the driver and the pickup sensor, which face the part, may be shaped according to the shape of the part to achieve better coupling therebetween.

Figure 6:
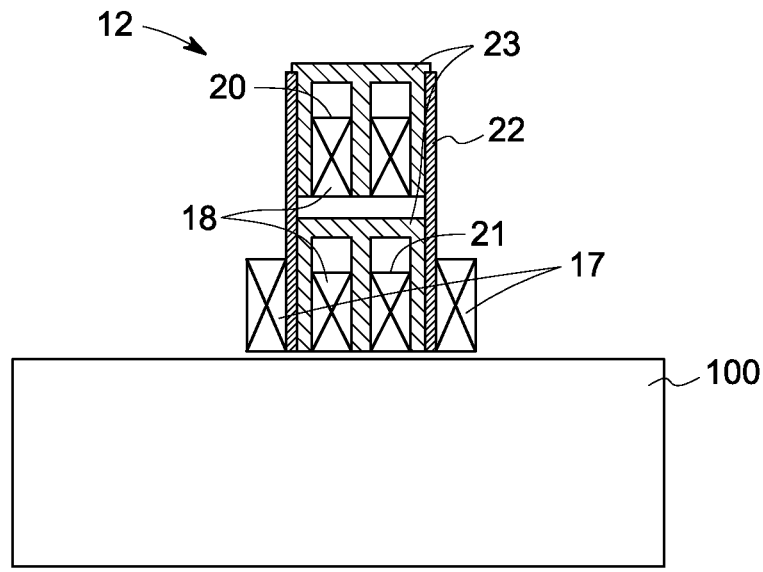

FIG. 6 is a schematic cross sectional diagram of an example arrangement of the eddy current 12 and the part 100. For the illustrated arrangement, the eddy current probe 12 faces a local area (not labeled) of the part 100, and comprises a driver 17 and a pair of pickup sensors 18.

The driver 17 extends around the pair of pickup sensors 18 are disposed through, and comprises an upper pickup sensor 20 and a lower pickup sensor 21 disposed beneath the upper pickup sensor 20. In one non-limiting example, the bottom surfaces of the driver 17 and the lower pickup sensor 21 may be located within the same plane to face a local area of the part 100. A pair of magnet cores 23 may be disposed through and around the periphery of the upper and lower pickup sensors 20 and 21, respectively. Additionally, a magnetic shield 22 may be disposed between and separate the driver 17 and the pickup sensors 18 to converge the magnetic flux of the pickup sensors 20, 21 and to avoid interactive interference of the signals from the driver 17 and the pickup sensors 20, 21.

In non-limiting examples, the driver 17 and the pair of pickup sensors 18 may have cylindrical hollow shapes. Alternatively, the driver 17 and the pickup sensors 18 may have other shapes to cooperate with the part 100 based on different applications.

Accordingly, during operation, the driver 17 receives a plurality of excitation signals with different frequencies from the function generator or the pulse generator 11 (shown in FIGS. 1-2) to induce the eddy currents in the part 100. The lower pickup sensor 21 senses the eddy currents and outputs one or more response signals into the processor 13. Meanwhile, the upper pickup sensor 21 senses the eddy currents and noise signals in ambient environment, and outputs signals into the processor 13. The processor 13 analyzes the signals from the upper and lower pickup sensors 20, 21 to improve the measurement accuracy of the case hardening depth of the local area of the part 100.

Figure 7:
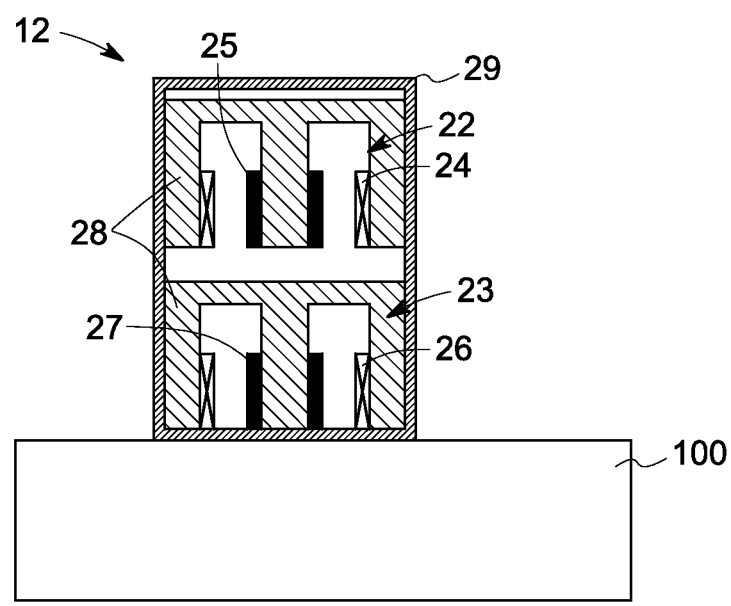

FIG. 7 is a schematic cross sectional diagram of an example arrangement of the eddy current probe 12 and the part 100 in accordance with another embodiment of the invention. For the illustrated arrangement, the eddy current probe 12 comprises an upper assembly 22 and a lower assembly 23 disposed beneath the upper assembly 22. The upper assembly 22 comprises an upper driver 24 and an upper pickup sensor 25. The lower assembly 23 comprises a lower driver 26 and a lower pickup sensor 27. The lower and upper drivers extend around the lower and upper pickup sensors respectively.

In some examples, two magnet cores 28 may or may not be disposed through the lower and upper pickup sensors and around the peripheries of the upper and lower drivers, respectively. Further, a magnetic shield 29 may be provided to enclose the upper and lower assemblies 22, 23. In certain applications, the drivers and pickup sensors may have cylindrical hollow shapes or other shapes.

Alternatively, in certain examples, the numerals 24 and 26 may indicate the pickup sensors, and the numerals 25 and 27 may indicate the drivers.

Figure 8:
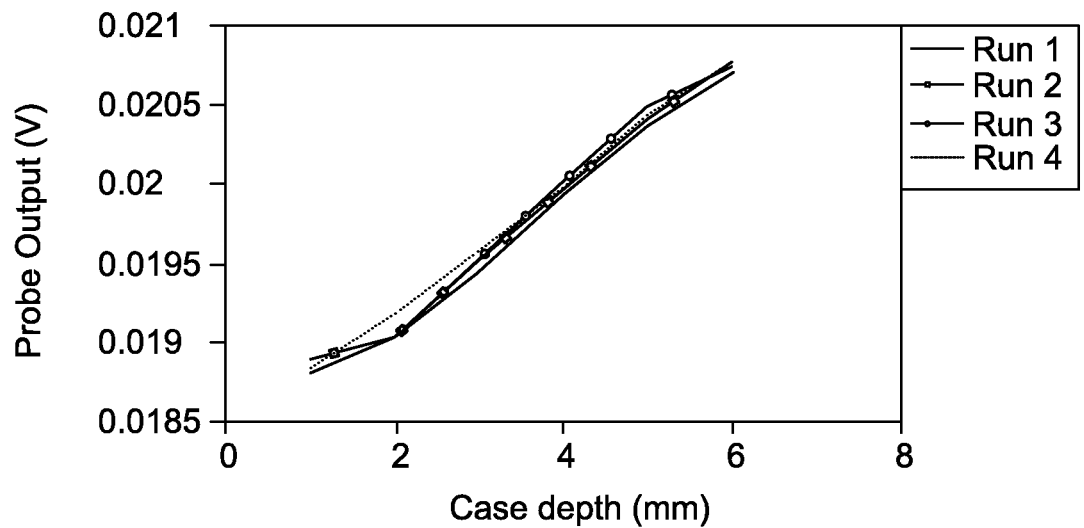
FIG. 8 shows example experimental data obtained using the eddy current inspection system shown in FIG. 1.

FIG. 8 shows an example experimental data obtained using the MFEC inspection system (shown in FIG. 1) for inspection of a set of specimens (not shown). As illustrated in FIG. 8, for retrieval of the experimental data, the example eddy current probe 12 shown in FIG. 7 may be provided in the MFEC inspection system. In one example, outer diameters of the drivers 24 and 26 were 16 mm. The set of the specimens had predetermined respective case hardening depths, for example 1 mm, 2 mm, 3 mm, 4 mm, 5 mm, and 6 mm. A 120 Hz excitation signal was input into the eddy current probe 12 to perform four measurements (as indicated in FIG. 8 via runs 1-4) on the same set of the specimens so as to retrieve the example experimental data.

For the example experimental data, the curves retrieved from the four measurements had similar curvatures, so that the four measurements were repeatable, thus indicating a stable correlation between the predetermined case hardening depth values and respective measured case hardening depth values retrieved from the MFEC system. Variations between respective measurement values retrieved from the same specimen were smaller than the differences between measured values retrieved from the specimens with different case hardening depths, thus indicating that the probe response signals due to case hardening depth changes were larger than the probe response signals due to noise factors, such as probe positioning differences, lift off effects, angles, and other undesired differences in the specimens. Accordingly, the data illustrates the suitability of the MFEC system for case hardening depth measurements. In some examples, the data may be analyzed using a multi-frequency phase analysis (MFPA) algorithm for compensation of the noise factors, such as lift off effects.

Figure 9:
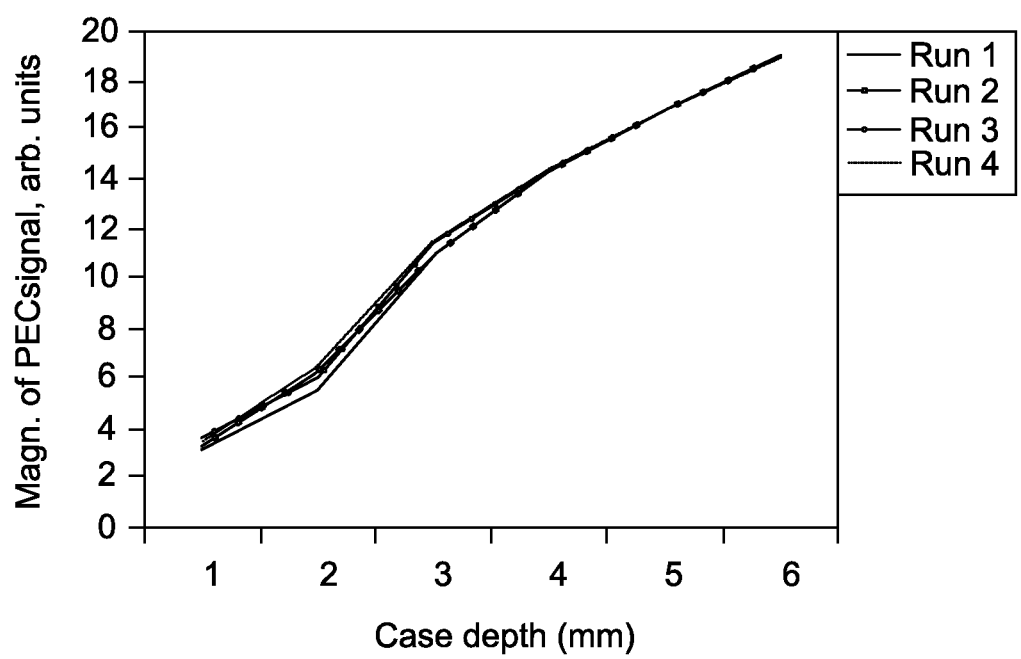
FIG. 9 shows example experimental data obtained using the eddy current inspection system shown in FIG. 2.

FIG. 9 shows an example experimental data obtained using the PEC inspection system (shown in FIG. 2) for inspection of a set of specimens (not shown). As illustrated in FIG. 9, for retrieval of the experimental data, the example eddy current probe 12 shown in FIG. 4 may be provided in the PEC inspection system. In one example, outer diameters of the drive 17 and the pickup sensor 18 were 20 mm, respectively. The set of the specimens had predetermined respective case hardening depths, for example 1 mm, 2 mm, 3 mm, 4 mm, 5 mm, and 6 mm.

Similar to the data shown in FIG. 8, a 95 Hz excitation signal was input into the eddy current probe 12 to perform four measurements (as indicated in FIG. 9 via runs 1-4) on the same set of the specimens so as to retrieve the example experimental data.

For the example experimental data, the curves retrieved from the four measurements had similar curvatures, so that the four measurements are repeatable, thus indicating a stable correlation between the predetermined case hardening depth values and the respective measured case hardening depth values retrieved from the PEC system. Variations between the respective measurement values retrieved from the same specimen were smaller than the differences between the measured values retrieved from the specimens with different case hardening depths, thus indicating that the probe response signals due to case hardening depth changes were larger than the probe response signals due to noise factors, such as probe positioning differences, lift off effects, angles, and other undesired differences in the specimens. Accordingly, the data illustrates the suitability of the PEC system for case hardening depth measurements. In some examples, the data may be analyzed using a multi-frequency phase analysis (MFPA) algorithm for compensation of the noise factors, such as lift off variations.

Figure 10:
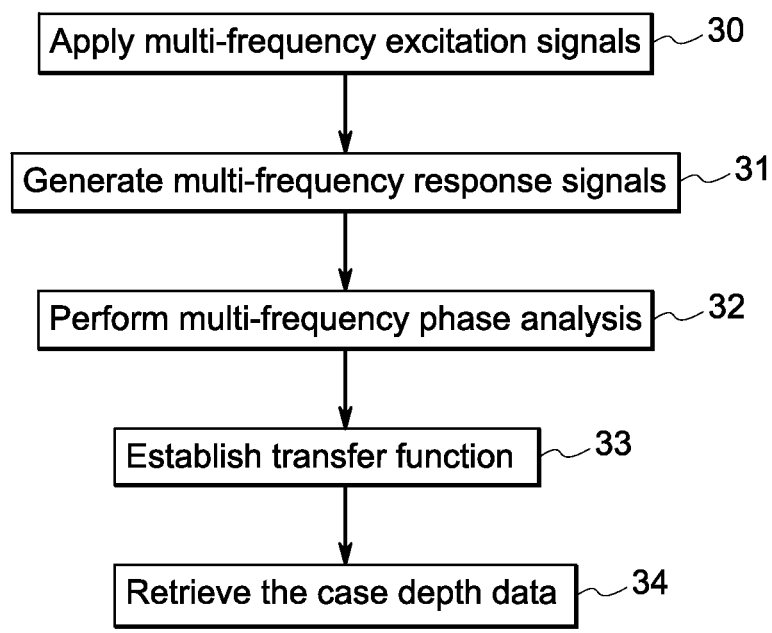
FIG. 10 is a flow chart schematically illustrating measurement of case hardening depth of a part.

FIG. 10 is a flow chart schematically illustrating the measurement of the case hardening depth of the part 100. As depicted in FIG. 10, in step 30, a plurality of excitation signals with different frequencies from the function generator or the pulse generator 11 are applied to the eddy current probe 12 to induce eddy currents in the inspection part 100. Then, in step 31, multi-frequency response signals are generated. The number of frequencies needed for the generation of the multi-frequency response signals, may be selected based on the number of undesired noise features to be eliminated. In one example, the generated multi-frequency response signals are included in a multi-frequency response dataset. As used herein, the term "multi-frequency response dataset" refers to a dataset that comprises an entire set of response signals that are generated as a result of the eddy current induced in the inspection part under consideration by application of the multi-frequency excitation signals to the eddy current probe.

Next, in step 32, the controller 13 analyzes the multi-frequency response signals using the multi-frequency phase analysis to suppress the noise factors, such as lift off effects and to determine a plurality of MFPA parameters. Other details of the multi-frequency phase analysis may be found, for example in U.S. Pat. No. 7,206,706.

Subsequently, in step 33, based on the multi-frequency analysis of the multi-frequency response signals, a transfer function is established, which can be readily implemented by one skilled in the art. Finally, in step 34, based on the transfer function and the MFPA parameters, the case hardening depths of the part may be retrieved.

While the disclosure has been illustrated and described in typical embodiments, it is not intended to be limited to the details shown, since various modifications and substitutions can be made without departing in any way from the spirit of the present disclosure. As such, further modifications and equivalents of the disclosure herein disclosed may occur to persons skilled in the art using no more than routine experimentation, and all such modifications and equivalents are believed to be through the spirit and scope of the disclosure as defined by the subsequent claims.

What is claimed is:

1. A multi-frequency eddy current (MFEC) inspection system for inspection of case hardening depth on a part, the MFEC inspection system comprising:
a generator configured to generate one or more multi-frequency excitation signals, wherein the generator comprises a function generator;
an eddy current probe configured to be disposed at one side of the part and comprising one or more drivers and one or more pickup sensors, wherein the one or more drivers are configured to receive the one or more multi-frequency excitation signals to induce eddy currents in the part and the one or more pickup sensors are configured to detect the induced eddy currents within a local area of the part to generate one or more multi-frequency response signals; and
a processor configured to receive the one or more multi-frequency response signals for processing to determine a case hardening depth of the local area of the part, wherein the processor comprises a lock-in amplifier, and
wherein the function generator is further configured to supply one or more reference signals with the same frequencies as the respective one or more multi-frequency response signals to the lock-in amplifier.

2. The MFEC inspection system of claim 1, wherein the one or more drivers and the one or more pickup sensors comprise windings, and wherein each of the one or more drivers and the one or more pickup sensors has a cylindrical shape or a rectangular shape.

3. The MFEC inspection system of claim 1, wherein the one or more pickup sensors comprise one or more solid-state magnetic sensors, and wherein the one or more solid-state magnetic sensors comprises one or more of an anisotropic magnetoresistance (AMR) sensor, a giant magnetoresistance (GMR) sensor, a tunneling magnetoresistance (TMR), an extraordinary magnetoresistance (EMR) sensor, a giant magnetoimpedance (GMI), and a Hall sensor.

4. The MFEC inspection system of claim 3, wherein each of the one or more drivers and the one or more pickup sensors has a cylindrical shape, wherein the part has a cylindrical shape, and wherein at least one axis of one of the one or more drivers and the one or more pickup sensors is parallel to an axis of the part.

5. The MFEC inspection system of claim 1, wherein the one or more drivers and the one or more pickup sensors comprise at least one respective surface configured to face the local area of the part directly, and wherein the at least two respective surfaces of the one or more drivers and the one or more pickup sensors are coplanar or have an angle therebetween.

6. The MFEC inspection system of claim 1, wherein each of the one or more pickup sensors comprise an upper pickup sensor and a lower pickup sensor disposed below the upper pickup sensor, and wherein the surfaces of the one or more drivers and the lower pickup sensor are configured to face the local area of the part directly.

7. The MFEC inspection system of claim 6, wherein each of the one or more drivers comprise an upper driver and a lower driver disposed below the upper driver, and wherein the surfaces of the lower driver and the lower pickup sensor face the local area of the part directly.

8. The MFEC inspection system of claim 7, wherein each of the one or more drivers comprise an upper driver and a lower driver disposed below the upper driver, and wherein the surfaces of the lower driver and the lower pickup sensor face the local area of the part directly.

9. A method for inspection of case hardening depth on a part, the method comprising:
  generating one or more multi-frequency excitation signals or one or more pulse excitation signals;
  providing an eddy current probe configured to be disposed at one side of the part to receive the one or more multi-frequency excitation signals or the one or more pulse excitation signals and output one or more multi-frequency response signals, wherein the eddy current probe comprises one or more drivers and one or more pickup sensors, wherein the one or more drivers are configured to receive the one or more multi-frequency excitation signals to induce eddy currents in the part, and wherein the one or more pickup sensors are configured to detect the induced eddy currents within a local area of the part to generate the one or more multi-frequency response signals; and
  processing the one or more multi-frequency response signals to determine the case hardening depth of the local area of the part,
  wherein each of the one or more drivers and the one or more pickup sensors has a cylindrical shape, wherein the part has a cylindrical shape, and wherein at least one axis of one of the one or more drivers and the one or more pickup sensors is parallel to an axis of the part.

10. The method of claim 9, wherein the one or more multi-frequency excitation signals are generated using a function generator, wherein the one or more pulse excitation signals are generated using a pulse generator, and wherein a lock-in amplifier is provided to process the one or more multi-frequency response signals when the function generator is provided.

11. The method of claim 9, wherein the one or more multi-frequency response signals are processed using a multi-frequency analysis algorithm to determine the case hardening depth on the local area of the part.

12. An inspection system for inspection of case hardening depth on a part, the inspection system comprising:
  a generator configured to generate one or more multi-frequency excitation signals or one or more pulse excitation signals;
  an eddy current probe configured to be disposed at one side of the part and comprising one or more drivers and one or more pickup sensors, wherein the one or more drivers are configured to receive the one or more multi-frequency excitation signals or the one or more pulse excitation signals to induce eddy currents in the part and the one or more pickup sensors are configured to detect the induced eddy currents within a local area of the part to generate one or more multi-frequency response signals; and
  a processor configured to receive the one or more multi-frequency response signals for processing to determine a case hardening depth of the local area of the part;
  wherein the one or more pickup sensors comprise one or more solid-state magnetic sensors, and wherein the one or more solid-state magnetic sensors comprises one or more of an anisotropic magnetoresistance (AMR) sensor, a giant magnetoresistance (GMR) sensor, a tunneling magnetoresistance (TMR), an extraordinary magnetoresistance (EMR) sensor, a giant magnetoimpedance (GMI), and a Hall sensor.

13. The inspection system of claim 12, wherein the generator comprises a function generator or a pulse generator.

14. The inspection system of claim 12, wherein each of the one or more drivers and the one or more pickup sensors has a cylindrical shape, wherein the part has a cylindrical shape, and wherein at least one axis of one of the one or more drivers and the one or more pickup sensors is parallel to an axis of the part.

15. An inspection system for inspection of case hardening depth on a part, the inspection system comprising:
  a generator configured to generate one or more multi-frequency excitation signals or one or more pulse excitation signals;
  an eddy current probe configured to be disposed at one side of the part and comprising one or more drivers and one or more pickup sensors, wherein the one or more drivers are configured to receive the one or more multi-frequency excitation signals or the one or more pulse excitation signals to induce eddy currents in the part and the one or more pickup sensors are configured to detect the induced eddy currents within a local area of the part to generate one or more multi-frequency response signals; and
  a processor configured to receive the one or more multi-frequency response signals for processing to determine a case hardening depth of the local area of the part;
  wherein the one or more drivers and the one or more pickup sensors comprise at least one respective surface configured to face the local area of the part directly, and wherein the at least two respective surfaces of the one or more drivers and the one or more pickup sensors are coplanar or have an angle therebetween.

16. The inspection system of claim 15, wherein the generator comprises a function generator or a pulse generator.

17. The inspection system of claim 15, wherein each of the one or more pickup sensors comprise an upper pickup sensor and a lower pickup sensor disposed below the upper pickup sensor, and wherein the surfaces of the one or more drivers and the lower pickup sensor are configured to face the local area of the part directly.

18. The inspection system of claim 17, wherein each of the one or more drivers comprise an upper driver and a lower driver disposed below the upper driver, and wherein the surfaces of the lower driver and the lower pickup sensor face the local area of the part directly.

* * * * *